United States Patent
Moller

(10) Patent No.: US 9,132,243 B2
(45) Date of Patent: Sep. 15, 2015

(54) METHOD OF ADMINISTERING A SUBSTANCE TO THE THROAT

(75) Inventor: Rene Arnfoldt Moller, Holte (DK)

(73) Assignee: TannerMedico A/S, Horsholm (DK)

( * ) Notice: Subject to any disclaimer, the term of this patent is extended or adjusted under 35 U.S.C. 154(b) by 0 days.

(21) Appl. No.: 12/842,267

(22) Filed: Jul. 23, 2010

(65) Prior Publication Data

US 2012/0017898 A1 Jan. 26, 2012

(51) Int. Cl.
  *A61F 5/56* (2006.01)
  *A61M 15/00* (2006.01)
  *A61M 11/00* (2006.01)
  *A61M 15/08* (2006.01)

(52) U.S. Cl.
  CPC .................. *A61M 11/00* (2013.01); *A61F 5/56* (2013.01); *A61M 11/008* (2014.02); *A61M 15/0031* (2014.02); *A61M 15/0051* (2014.02); *A61M 15/08* (2013.01)

(58) Field of Classification Search
  CPC ............ A61K 2300/00; A61K 9/0043; A61M 15/009; A61M 15/08; A61M 11/00; A61M 11/06; A61M 15/0028
  USPC ........... 128/203.12, 200.22; 514/179; 604/36, 604/37, 94.01, 185, 212, 264, 295; 222/129, 541.6, 153.07, 153.06, 420, 222/541.1, 541.4, 541.9, 210; 206/438
  See application file for complete search history.

(56) References Cited

U.S. PATENT DOCUMENTS

| | | | |
|---|---|---|---|
| 3,782,066 A | 1/1974 | Schmitt | |
| 6,062,213 A | 5/2000 | Fuisz et al. | |
| 6,241,124 B1* | 6/2001 | Hoyt | 222/143 |
| 6,383,166 B1 | 5/2002 | Farris | |
| 7,163,013 B2 | 1/2007 | Harrison | |
| 8,003,353 B2* | 8/2011 | Quay et al. | 435/86 |
| 2005/0028813 A1 | 2/2005 | Harrison | |
| 2009/0071108 A1* | 3/2009 | Nelson et al. | 53/453 |
| 2009/0312724 A1* | 12/2009 | Pipkin et al. | 604/294 |
| 2010/0040712 A1 | 2/2010 | Fisher et al. | |
| 2010/0089952 A1* | 4/2010 | Cleary et al. | 222/215 |
| 2010/0193380 A1* | 8/2010 | Sullivan et al. | 206/219 |

* cited by examiner

*Primary Examiner* — Tan-Uyen (Jackie) T Ho
*Assistant Examiner* — Mark Wardas
(74) *Attorney, Agent, or Firm* — Nordic Patent Service

(57) ABSTRACT

A pharmaceutical product in the form of an anti-snoring substance includes a container containing the anti-snoring substance, the anti-snoring substance being in the form of a solution pre-concentrate. The container is made by a blow-fill-seal technology, wherein the container material is Polyethylene or Polypropylene. The container includes a body portion containing the anti-snoring substance and a fluid outlet portion configured to deliver the anti-snoring substance.

2 Claims, 2 Drawing Sheets

GROUND

METHOD OF ADMINISTERING A SUBSTANCE TO THE THROAT

BACKGROUND OF THE INVENTION

The present disclosure generally relates to administering a substance to the throat. More particularly, the aspects of the disclosed embodiments relate to administering a substance to the throat via the nose using a blow-fill-mold style bottle.

Devices are available for administering active substances or substances to the body, particularly through the throat, lungs or sinuses. These devices generally include containers that have a main chamber holding the desired contents and a head portion that is inserted into the nose or mouth. By squeezing the container, the substance is released into the nose or mouth. In some cases, the device has a tab or seal that must be broken in order to release the substance. A relatively narrow neck on the device can form the outlet channel from the main chamber into the head portion. This outlet channel can sealed by a frangible membrane that is typically formed by placing a crimp, tab or seal across the head portion during the molding and sealing process. At the time of use, the head portion is broken away from the main chamber portion, thus opening the outlet channel and allowing removal or dispensing of the contents. When the substance is being administered orally, the user will typically inhale at roughly the same time as the substance is released in order to force the medicine into, or further into, the sinus cavity, throat or lungs.

The blow-fill-seal process (BFS process), also referred to herein as blow-fill-mold, is a single operation which produces sterile containers. Bottles or vials made from materials such as from thermoplastic, are blown to a desired shape and immediately on cooling are filled aseptically with a desired fluid and hermetically sealed. The containers that are produced by the blow-fill-seal process are generally referred to herein as "BFS containers." The blow-fill seal process generally produces compact, easy-to-use substance dispensing devices that can be used to deliver substance to the throat, lungs or sinuses.

Snoring is a serious problem for a large segment of the population. Snoring is a sleep disorder that can range from mild to severe in humans. Mild cases may result in no more than fitful sleep by the sufferer, while severe cases can cause disturbance of the sleep of others, and may result in insufficient inhalation of oxygen by the sufferer, apnea and, in extreme cases, death.

Remedies to alleviate the symptoms of snoring can range from surgery to a variety of substances. Although surgery has been proven to be somewhat effective, it is a radical and expensive approach that is subject to all the usual risks associated with surgery. Drugs are available by prescription for the treatment of the symptoms of snoring. Other snoring management techniques can include for example, mechanical aids, nasal strips and anti-snoring sprays. Anti-snoring sprays can tend to be ineffective unless applied repeatedly during the night. Additionally, device sterilization is a concern when administering anti-snoring sprays due to the potential for infection since the sprays are introduced directly into the lungs in a manner that at least partially bypasses the patient's natural defense mechanisms.

Accordingly, it would be desirable to provide a system that addresses at least some of the problems identified above.

BRIEF DESCRIPTION OF THE INVENTION

As described herein, the exemplary embodiments of the present invention overcome one or more of the above or other disadvantages known in the art.

In one aspect, the disclosed embodiments are directed to a pharmaceutical product in the form of an anti-snoring substance. In one embodiment, the product includes a container containing the anti-snoring substance; the anti-snoring substance being in the form of a solution pre-concentrate; the container being made by a blow-fill-seal technology, wherein the container material is Polyethylene or Polypropylene; the container including a body portion containing the anti-snoring substance and a fluid outlet portion configured to deliver the anti-snoring substance.

In another aspect, the disclosed embodiments are directed to a method for administering an anti-snoring substance. In one embodiment, the method includes sealing a unit dose of the anti-snoring substance in a container made by a blow-fill-seal technology; opening the unit dose; administering the anti-snoring substance to a nasal passage of a patient while a head of the patient is in a substantially backward tilted position in order for the substance to reach a throat of the patient, wherein the anti-snoring substance is delivered into the nasal passage in the form of a jet stream.

In a further aspect, the disclosed embodiments are directed to a nasal spray apparatus. In one embodiment, the apparatus includes a nasal preparation containing an anti-snoring substance; a container having an opening that provides access to an interior cavity, which container is operable to hold the anti-snoring substance within the interior cavity; a pump dispenser mounted on the container in a manner that closes the opening; wherein the container and pump dispenser are manufactured by a blow-fill-mold process.

These and other aspects and advantages of the disclosed embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Moreover, the drawings are not necessarily drawn to scale and that, unless otherwise indicated, they are merely intended to conceptually illustrate the structures and procedures described herein.

DETAILED DESCRIPTION OF THE EXEMPLARY EMBODIMENTS OF THE INVENTION

Figure 1:
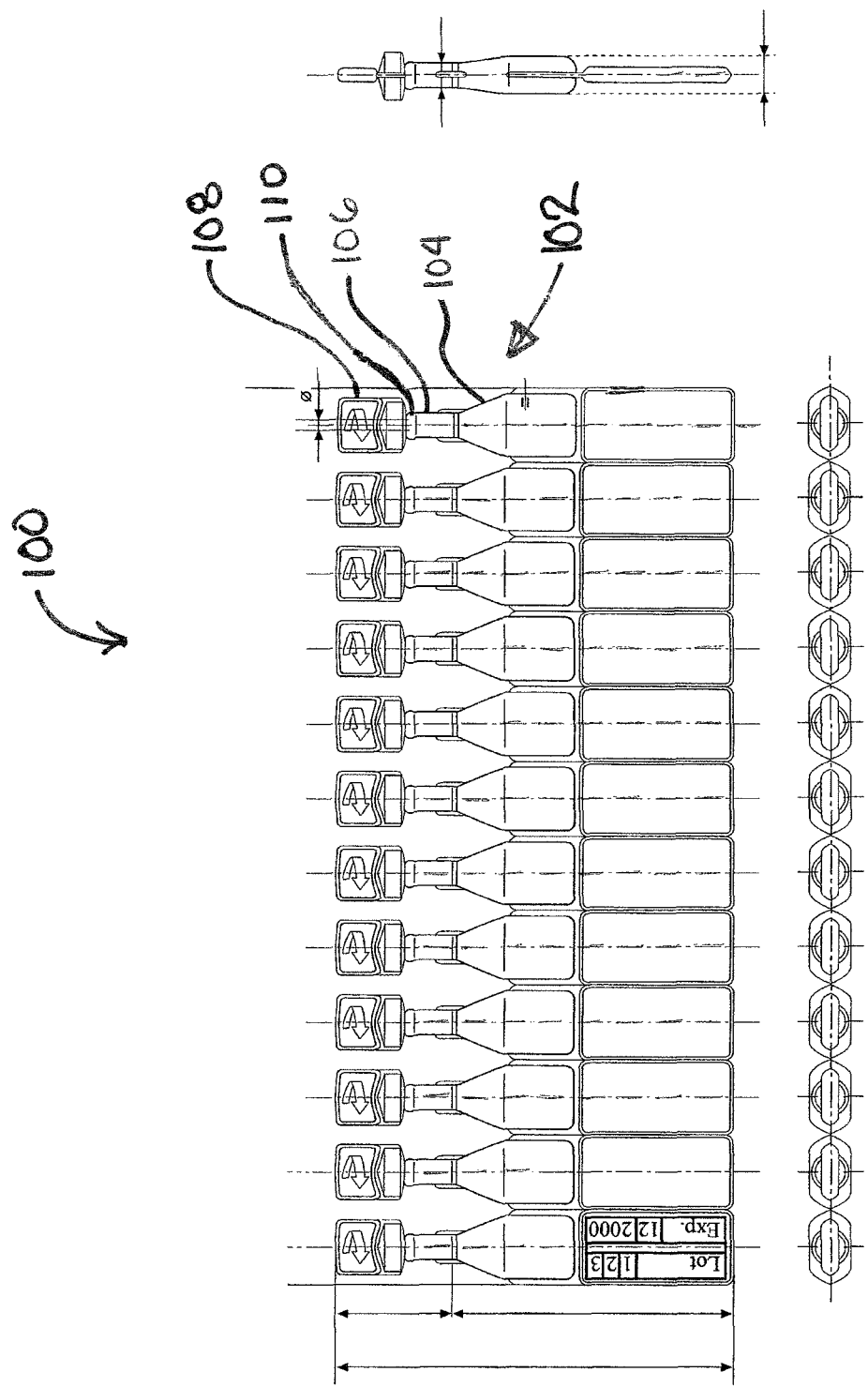
FIG. 1 illustrates an exemplary dispensing device incorporating aspects of the present disclosure.

Referring now to FIG. 1, a device 102 for the nasal or oral delivery of a substance is shown. The aspects of the disclosed embodiments are generally directed to the administration of an anti-snoring substance or medicament to a patient with a device manufactured using blow-fill-seal or blow-fill-mold technology. The device 102 shown in FIG. 1 is part of an ampule pack 100. In one embodiment, the device 102 comprises a sealed flexible container or body portion 104 containing the substance or medicament. The device 102 is typically manufactured using a blow-fill-seal or blow-fill-mold technique.

As shown in FIG. 1, the device 102 generally comprises a body portion 104 and a fluid outlet portion 106. The body portion 104 is configured to hold the nasal preparation, also referred to herein as the anti-snoring substance. In one embodiment, the device 102 includes a tab portion 108, which is generally configured to be of a twist off type. A frangible member 110 can be included on the fluid outlet portion 106 near or as part of the tab portion 108, to allow the tab portion 108 to be easily removed.

Figure 2:
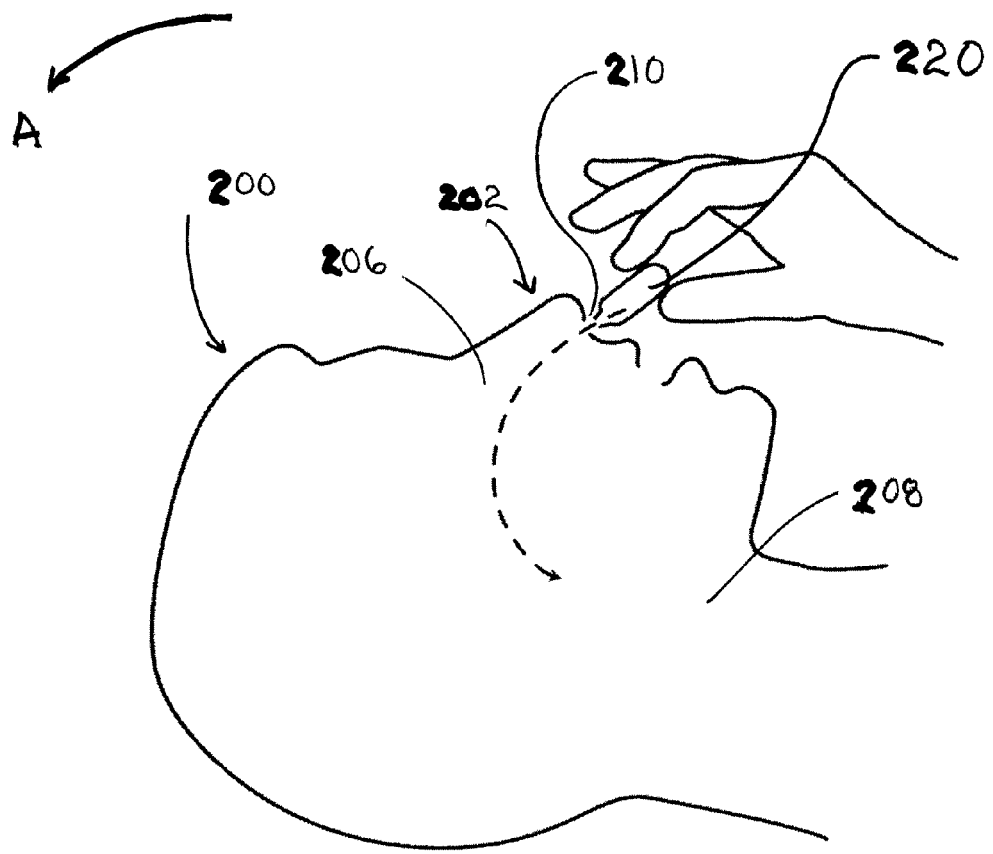
FIG. 2 illustrates a use application of the dispensing device incorporating aspects of the disclosed embodiments.

During the blow-fill-seal process, the device 102 is substantially filled with the anti-snoring substance when oriented in the vertical plane and sealed. When the tab 108 is removed, the substance can be dispensed, such as shown in FIG. 2. In this embodiment, the substance is generally dispensed by allowing the substance to exit from the fluid outlet portion 106 as the device 102 is positioned with the fluid outlet portion 106 oriented in a substantially downward direction. In this example, the body portion 104 can be compressed to force or urge the substance from the body portion 104 and out of the fluid outlet portion 106 in the form of a jet stream, rather than a spray or atomization.

In one embodiment, the substance comprises an anti-snoring solution named ASONOR® and manufactured by TannerMedico NS, Denmark. The solution contains Sodium Chloride, Glycerol, Polysorbate and Edetatesodium. Potassium sorbate can be added as preservative. During the manufacturing process, the solution is filled into the body portion 104 as part of the Blow-Fill-Seal process, as otherwise known in the art. In one embodiment, the containers 102 are plastic Polypropylene or Polyethylene containers. In alternate embodiments, the containers 102 can comprise any suitable container for use in the Blow-Fill-Seal process. Each container forms a single unit dose.

A method of administering the substance according to one aspect of the disclosed embodiments is described with respect to FIG. 2. As shown in FIG. 2, the head 200 of the user is generally tilted in a backwards or rearwards direction, such as the direction A shown in FIG. 2, from a substantially upright position, so that the nose 202 is in a substantially horizontal or slightly backward tilted position relative to the ground 204. Generally, the head 200 needs to be tilted backwards far enough, for a period of time, to allow the substance to travel through the nasal passages 206 to the throat area 208. By tilting the head 200 backwards, gravity will assist in delivering the liquid substance to the throat area 208 through the nasal passages 206.

Once the head 200 is in the tilted back position as is shown in FIG. 2, the end 106 of device 100 being used is placed in or near the opening of the nostril 210. The container 220 is then squeezed to deliver the substance into the nasal passage 206 and to the throat passage 208. The container 220 is squeezed a sufficient number of times until the substance is felt in the throat passage 208 or the entire substance is expended. The process is repeated for each of the nasal passages 206. Generally, three to four pumps into each nostril 210 is sufficient.

The liquid substance is not intended to remain in the nasal passages 206, as the benefits of this anti-snoring substance are primarily realized from the substance reaching the throat passage 208.

The aspects of the disclosed embodiments provide an effective treatment against snoring. An anti-snoring substance, and in particular ASONOR®, is administered into the nasal passages using a blow-fill mold style bottle. By incorporating a jet-stream style outlet nozzle, rather than a spray or atomization, the substance does not stay in the nose, but is rather delivered to the throat. This advantageously allows the substance to begin working sooner.

Moreover, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method of administering an anti-snoring substance to a patient, comprising:
   sealing a unit dose of the anti-snoring substance in a container made by a blow-fill-seal technology, the anti-snoring substance comprising sodium chloride, glycerol, polysorbate and edetatesodium;
   opening the unit dose;
   administering the anti-snoring substance to a nasal passage of the patient while a head of the patient is in a substantially backward tilted position in order for the substance to reach a throat of the patient, wherein an anti-snoring effective amount of the anti-snoring substance is delivered to a throat passage of the patient through the nasal passage in the form of a jet stream.

2. The method of claim 1 wherein the anti-snoring substance is administered by squeezing the container.

* * * * *